(12) United States Patent
Pavento et al.

(10) Patent No.: US 11,071,634 B2
(45) Date of Patent: *Jul. 27, 2021

(54) NUBBED PLATE

(71) Applicant: DePuy Synthes Products, Inc., Raynham, MA (US)

(72) Inventors: Nicholas Pavento, North Attleboro, MA (US); John Riley Hawkins, Cumberland, RI (US); Sheryl Furlan, Middleboro, MA (US); Douglas Raymond, Bridgewater, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 95 days.

This patent is subject to a terminal disclaimer.

(21) Appl. No.: 16/414,064

(22) Filed: May 16, 2019

(65) Prior Publication Data
US 2019/0269522 A1 Sep. 5, 2019

Related U.S. Application Data

(63) Continuation of application No. 15/846,344, filed on Dec. 19, 2017, now Pat. No. 10,327,915, which is a
(Continued)

(51) Int. Cl.
*A61F 2/44* (2006.01)
*A61B 17/70* (2006.01)
(Continued)

(52) U.S. Cl.
CPC .......... *A61F 2/447* (2013.01); *A61B 17/7059* (2013.01); *A61F 2/30744* (2013.01);
(Continued)

(58) Field of Classification Search
CPC ........ A61F 2/44; A61F 2/4425; A61F 2/4435; A61F 2/447; A61F 2/4475
(Continued)

(56) References Cited

U.S. PATENT DOCUMENTS 1,636,636 A 7/1927 Humble
1,677,337 A 7/1928 Grove
(Continued)

FOREIGN PATENT DOCUMENTS

CN 201244104 Y 5/2009
DE 19710392 C1 7/1999
(Continued)

OTHER PUBLICATIONS

Allcock, "Polyphosphazenes", The Encyclopedia of Polymer Science, vol. 13, pp. 31-41, Wiley Intersciences, John Wiley & Sons, (1988).
(Continued)

*Primary Examiner* — Eric S Gibson
(74) *Attorney, Agent, or Firm* — BakerHostetler

(57) ABSTRACT

A separate nub component between the plate and an intervertebral fusion cage, wherein the nub is attached to the plate. The nub lessens the undesired pivotal movement of the plate. It is believed that when the nub fits snugly between the endplates of the adjacent vertebral bodies, it acts as a stop against the undesired pivotal movement of the plate.

20 Claims, 7 Drawing Sheets

Related U.S. Application Data continuation of application No. 15/581,571, filed on Apr. 28, 2017, now Pat. No. 9,872,781, which is a continuation of application No. 14/845,481, filed on Sep. 4, 2015, now Pat. No. 9,668,877, which is a continuation of application No. 13/413,264, filed on Mar. 6, 2012, now Pat. No. 9,271,836.

(51) Int. Cl.
*A61F 2/30* (2006.01)
*A61F 2/28* (2006.01)

(52) U.S. Cl.
CPC ............ *A61F 2/442* (2013.01); *A61F 2/4455* (2013.01); *A61F 2/30965* (2013.01); *A61F 2/4465* (2013.01); *A61F 2002/2817* (2013.01); *A61F 2002/2835* (2013.01); *A61F 2002/305* (2013.01); *A61F 2002/30378* (2013.01); *A61F 2002/30428* (2013.01); *A61F 2002/30482* (2013.01); *A61F 2002/30578* (2013.01); *A61F 2002/30593* (2013.01); *A61F 2002/30594* (2013.01); *A61F 2002/30604* (2013.01); *A61F 2002/30607* (2013.01); *A61F 2002/30616* (2013.01); *A61F 2002/30622* (2013.01); *A61F 2002/30774* (2013.01); *A61F 2002/30784* (2013.01); *A61F 2002/30785* (2013.01); *A61F 2002/30787* (2013.01); *A61F 2002/30836* (2013.01); *A61F 2002/30843* (2013.01); *A61F 2002/448* (2013.01); *A61F 2220/0008* (2013.01); *A61F 2310/00011* (2013.01); *A61F 2310/00017* (2013.01); *A61F 2310/00023* (2013.01); *A61F 2310/00029* (2013.01); *A61F 2310/00047* (2013.01); *A61F 2310/00053* (2013.01); *A61F 2310/00101* (2013.01); *A61F 2310/00161* (2013.01); *A61F 2310/00179* (2013.01); *A61F 2310/00203* (2013.01); *A61F 2310/00239* (2013.01); *A61F 2310/00359* (2013.01); *A61F 2310/00407* (2013.01)

(58) Field of Classification Search
USPC ................... 623/17.11–17.16; 606/99, 100
See application file for complete search history.

(56) References Cited

U.S. PATENT DOCUMENTS

| | | | |
|---|---|---|---|
| 2,304,703 A | 12/1942 | O'Leary | |
| 4,105,034 A | 8/1978 | Shalaby et al. | |
| 4,130,639 A | 12/1978 | Shalaby et al. | |
| 4,140,678 A | 2/1979 | Shalaby et al. | |
| 4,141,087 A | 2/1979 | Shalaby et al. | |
| 4,205,399 A | 6/1980 | Jamiolkowski et al. | |
| 4,208,511 A | 6/1980 | Jamiolkowski et al. | |
| 4,743,256 A | 5/1988 | Brantigan | |
| 4,904,261 A | 2/1990 | Dove et al. | |
| 4,955,908 A | 9/1990 | Frey et al. | |
| 5,041,113 A | 8/1991 | Biedermann et al. | |
| 5,123,926 A | 6/1992 | Pisharodi | |
| 5,147,361 A | 9/1992 | Ojima et al. | |
| 5,209,751 A | 5/1993 | Farris et al. | |
| 5,306,308 A | 4/1994 | Gross et al. | |
| 5,352,231 A | 10/1994 | Brumfield et al. | |
| 5,391,170 A | 2/1995 | McGuire et al. | |
| 5,395,372 A | 3/1995 | Holt et al. | |
| 5,397,364 A | 3/1995 | Kozak et al. | |
| 5,443,514 A | 8/1995 | Steffee | |
| 5,443,515 A | 8/1995 | Cohen et al. | |
| 5,464,407 A | 11/1995 | McGuire | |
| 5,464,929 A | 11/1995 | Bezwada et al. | |
| 5,499,986 A | 3/1996 | Dimarco | |
| 5,529,580 A | 6/1996 | Kusunoki et al. | |
| 5,534,031 A | 7/1996 | Matsuzaki et al. | |
| 5,578,034 A | 11/1996 | Estes | |
| 5,591,166 A * | 1/1997 | Bernhardt | A61B 17/7037 606/266 |
| 5,595,751 A | 1/1997 | Bezwada et al. | |
| 5,597,579 A | 1/1997 | Bezwada et al. | |
| 5,601,553 A | 2/1997 | Trebing et al. | |
| 5,607,687 A | 3/1997 | Bezwada et al. | |
| 5,609,636 A | 3/1997 | Kohrs et al. | |
| 5,618,552 A | 4/1997 | Bezwada et al. | |
| 5,620,458 A | 4/1997 | Green et al. | |
| 5,620,698 A | 4/1997 | Bezwada et al. | |
| 5,645,598 A | 7/1997 | Brosnahan, III | |
| 5,645,850 A | 7/1997 | Bezwada et al. | |
| 5,648,088 A | 7/1997 | Bezwada et al. | |
| 5,662,655 A | 9/1997 | Laboureau et al. | |
| 5,676,666 A | 10/1997 | Oxland et al. | |
| 5,698,213 A | 12/1997 | Jamiolkowski et al. | |
| 5,700,583 A | 12/1997 | Jamiolkowski et al. | |
| 5,713,899 A | 2/1998 | Marnay et al. | |
| 5,716,415 A | 2/1998 | Steffee | |
| 5,755,796 A * | 5/1998 | Ibo | A61F 2/4425 623/17.16 |
| 5,776,196 A | 7/1998 | Matsuzaki et al. | |
| 5,779,707 A | 7/1998 | Bertholet et al. | |
| 5,785,713 A | 7/1998 | Jobe | |
| 5,788,698 A | 8/1998 | Savornin | |
| 5,797,912 A | 8/1998 | Runciman et al. | |
| 5,797,918 A | 8/1998 | McGuire et al. | |
| 5,800,435 A * | 9/1998 | Errico | A61B 17/7007 606/261 |
| 5,800,440 A | 9/1998 | Stead | |
| 5,859,150 A | 1/1999 | Jamiolkowski et al. | |
| 5,888,223 A | 3/1999 | Bray, Jr. | |
| 5,904,689 A | 5/1999 | Jonjic | |
| 5,913,860 A | 6/1999 | Scholl | |
| 6,039,761 A | 3/2000 | Li et al. | |
| 6,049,026 A | 4/2000 | Muschler | |
| 6,056,749 A | 5/2000 | Kuslich | |
| 6,066,175 A * | 5/2000 | Henderson | A61F 2/44 623/17.11 |
| 6,086,593 A | 7/2000 | Bonutti | |
| 6,093,205 A | 7/2000 | McLeod et al. | |
| 6,099,531 A | 8/2000 | Bonutti | |
| 6,106,557 A | 8/2000 | Robioneck et al. | |
| 6,117,174 A | 9/2000 | Nolan | |
| 6,120,503 A | 9/2000 | Michelson | |
| 6,126,689 A | 10/2000 | Brett | |
| 6,127,597 A | 10/2000 | Beyar et al. | |
| 6,139,550 A | 10/2000 | Michelson | |
| 6,156,037 A * | 12/2000 | LeHuec | A61F 2/4637 606/247 |
| 6,159,211 A | 12/2000 | Boriani et al. | |
| 6,159,244 A | 12/2000 | Suddaby | |
| 6,174,311 B1 | 1/2001 | Branch et al. | |
| 6,179,875 B1 | 1/2001 | Von Strempel | |
| 6,190,414 B1 | 2/2001 | Young et al. | |
| 6,193,757 B1 | 2/2001 | Foley et al. | |
| 6,200,306 B1 | 3/2001 | Klostermeyer et al. | |
| 6,206,922 B1 | 3/2001 | Zdeblick et al. | |
| 6,224,602 B1 | 5/2001 | Hayes | |
| 6,231,610 B1 | 5/2001 | Geisler | |
| 6,235,059 B1 | 5/2001 | Benezech et al. | |
| 6,306,170 B2 | 10/2001 | Ray | |
| 6,330,845 B1 | 12/2001 | Meulink | |
| 6,336,928 B1 | 1/2002 | Guerin et al. | |
| 6,342,055 B1 | 1/2002 | Eisermann et al. | |
| 6,342,074 B1 | 1/2002 | Simpson | |
| 6,364,880 B1 | 4/2002 | Michelson | |
| 6,368,351 B1 | 4/2002 | Glenn et al. | |
| 6,375,462 B2 | 4/2002 | Holweg et al. | |
| 6,387,130 B1 | 5/2002 | Stone et al. | |
| 6,395,031 B1 | 5/2002 | Foley et al. | |
| 6,406,478 B1 | 6/2002 | Kuo | |
| 6,409,766 B1 | 6/2002 | Brett | |
| 6,413,278 B1 | 7/2002 | Marchosky | |
| 6,423,063 B1 | 7/2002 | Bonutti | |
| 6,428,575 B2 | 8/2002 | Koo et al. | |

(56) References Cited

U.S. PATENT DOCUMENTS

| | | | |
|---|---|---|---|
| 6,432,106 B1 * | 8/2002 | Fraser | A61F 2/30771 623/17.11 |
| 6,447,544 B1 | 9/2002 | Michelson | |
| 6,447,546 B1 | 9/2002 | Bramlet et al. | |
| 6,454,769 B2 | 9/2002 | Wagner et al. | |
| 6,461,359 B1 | 10/2002 | Tribus et al. | |
| 6,471,724 B2 | 10/2002 | Zdeblick et al. | |
| 6,488,710 B2 | 12/2002 | Besselink | |
| 6,508,818 B2 * | 1/2003 | Steiner | A61B 17/7007 606/71 |
| 6,558,387 B2 | 5/2003 | Errico et al. | |
| 6,558,423 B1 | 5/2003 | Michelson | |
| 6,562,073 B2 | 5/2003 | Foley | |
| 6,565,570 B2 | 5/2003 | Sterett et al. | |
| 6,572,619 B2 | 6/2003 | Santilli | |
| 6,579,290 B1 | 6/2003 | Hardcastle et al. | |
| 6,602,257 B1 | 8/2003 | Thramann | |
| 6,629,998 B1 | 10/2003 | Lin | |
| 6,672,977 B1 | 1/2004 | Colbo et al. | |
| 6,682,563 B2 | 1/2004 | Scharf | |
| 6,695,846 B2 | 2/2004 | Richelsoph et al. | |
| 6,730,125 B1 | 5/2004 | Lin | |
| 6,730,127 B2 | 5/2004 | Michelson | |
| 6,733,531 B1 | 5/2004 | Trieu | |
| 6,736,850 B2 | 5/2004 | Davis | |
| 6,743,257 B2 | 6/2004 | Castro | |
| 6,745,255 B2 | 6/2004 | Yen et al. | |
| 6,761,738 B1 | 7/2004 | Boyd | |
| 6,770,096 B2 | 8/2004 | Bolger et al. | |
| 6,773,437 B2 | 8/2004 | Ogilvie et al. | |
| 6,776,781 B1 | 8/2004 | Uwaydah | |
| 6,805,714 B2 | 10/2004 | Sutcliffe | |
| 6,808,537 B2 | 10/2004 | Michelson | |
| 6,824,564 B2 | 11/2004 | Crozet | |
| 6,824,565 B2 | 11/2004 | Muhanna et al. | |
| 6,833,006 B2 | 12/2004 | Foley et al. | |
| 6,835,208 B2 | 12/2004 | Marchosky | |
| 6,837,905 B1 | 1/2005 | Lieberman | |
| 6,849,093 B2 | 2/2005 | Michelson | |
| 6,890,335 B2 | 5/2005 | Grabowski et al. | |
| 6,890,355 B2 | 5/2005 | Michelson | |
| 6,945,973 B2 | 9/2005 | Bray | |
| 6,972,019 B2 | 12/2005 | Michelson | |
| 6,974,479 B2 | 12/2005 | Trieu | |
| 6,974,480 B2 | 12/2005 | Messerli et al. | |
| 6,984,234 B2 | 1/2006 | Bray | |
| 7,001,385 B2 | 2/2006 | Bonutti | |
| 7,033,394 B2 | 4/2006 | Michelson | |
| 7,041,135 B2 | 5/2006 | Michelson | |
| 7,044,971 B2 | 5/2006 | Suddaby | |
| 7,056,341 B2 | 6/2006 | Crozet | |
| 7,063,491 B2 | 6/2006 | French | |
| 7,070,598 B2 | 7/2006 | Lim et al. | |
| 7,077,864 B2 | 7/2006 | Byrd et al. | |
| 7,087,055 B2 | 8/2006 | Lim et al. | |
| 7,112,222 B2 | 9/2006 | Fraser et al. | |
| 7,112,223 B2 | 9/2006 | Davis | |
| 7,135,024 B2 | 11/2006 | Cook et al. | |
| 7,135,043 B2 | 11/2006 | Nakahara et al. | |
| 7,163,561 B2 | 1/2007 | Michelson | |
| 7,172,627 B2 | 2/2007 | Fiere et al. | |
| 7,226,482 B2 | 6/2007 | Messerli et al. | |
| 7,232,463 B2 | 6/2007 | Falahee | |
| 7,232,464 B2 | 6/2007 | Mathieu et al. | |
| 7,238,203 B2 | 7/2007 | Bagga et al. | |
| 7,238,206 B2 | 7/2007 | Lange et al. | |
| 7,255,698 B2 | 8/2007 | Michelson | |
| 7,276,081 B1 | 10/2007 | Coates et al. | |
| 7,288,094 B2 | 10/2007 | Lindemann et al. | |
| 7,288,095 B2 | 10/2007 | Baynham et al. | |
| 7,288,114 B2 | 10/2007 | Lange | |
| 7,306,605 B2 | 12/2007 | Ross | |
| 7,309,358 B2 | 12/2007 | Berry et al. | |
| 7,311,734 B2 | 12/2007 | Van et al. | |
| 7,316,714 B2 | 1/2008 | Gordon et al. | |
| 7,318,839 B2 | 1/2008 | Malberg et al. | |
| 7,323,011 B2 | 1/2008 | Shepard et al. | |
| 7,326,248 B2 | 2/2008 | Michelson | |
| 7,332,209 B2 | 2/2008 | Yokouchi et al. | |
| 7,338,525 B2 * | 3/2008 | Ferree | A61F 2/442 606/914 |
| 7,341,587 B2 | 3/2008 | Molz et al. | |
| 7,341,590 B2 | 3/2008 | Ferree | |
| 7,354,452 B2 | 4/2008 | Foley | |
| 7,361,193 B2 | 4/2008 | Frey et al. | |
| 7,435,262 B2 | 10/2008 | Michelson | |
| 7,438,715 B2 | 10/2008 | Doubler et al. | |
| 7,442,209 B2 | 10/2008 | Michelson | |
| 7,452,370 B2 | 11/2008 | Anderson | |
| 7,491,237 B2 | 2/2009 | Randall et al. | |
| 7,513,900 B2 | 4/2009 | Carrison et al. | |
| 7,527,641 B2 | 5/2009 | Suh | |
| 7,594,931 B2 | 9/2009 | Louis et al. | |
| 7,594,932 B2 | 9/2009 | Aferzon et al. | |
| 7,601,171 B2 * | 10/2009 | Ainsworth | A61B 17/70 623/17.11 |
| 7,601,173 B2 | 10/2009 | Messerli et al. | |
| 7,608,062 B2 | 10/2009 | Sweeney | |
| 7,618,456 B2 | 11/2009 | Mathieu et al. | |
| 7,628,816 B2 | 12/2009 | Magerl et al. | |
| 7,641,665 B2 | 1/2010 | Zubok et al. | |
| 7,655,042 B2 | 2/2010 | Foley et al. | |
| 7,658,766 B2 | 2/2010 | Melkent et al. | |
| 7,662,182 B2 | 2/2010 | Zubok et al. | |
| 7,674,279 B2 | 3/2010 | Johnson | |
| 7,704,255 B2 | 4/2010 | Michelson | |
| 7,726,002 B2 | 6/2010 | Shimp et al. | |
| 7,794,502 B2 | 9/2010 | Michelson | |
| 7,815,643 B2 | 10/2010 | Johnson et al. | |
| 7,815,681 B2 * | 10/2010 | Ferguson | A61F 2/4455 623/17.16 |
| 7,846,206 B2 | 12/2010 | Oglaza et al. | |
| 7,846,210 B2 | 12/2010 | Perez-Cruet et al. | |
| 7,862,616 B2 | 1/2011 | Lechmann et al. | |
| 7,871,441 B2 | 1/2011 | Eckman | |
| 7,875,062 B2 | 1/2011 | Lindemann et al. | |
| 7,875,076 B2 | 1/2011 | Mathieu et al. | |
| 7,883,531 B2 | 2/2011 | De Coninck | |
| 7,887,591 B2 | 2/2011 | Aebi et al. | |
| 7,887,595 B1 | 2/2011 | Pimenta | |
| 7,909,877 B2 | 3/2011 | Krueger et al. | |
| 7,993,403 B2 | 8/2011 | Foley et al. | |
| 8,002,808 B2 | 8/2011 | Morrison et al. | |
| 8,007,523 B2 | 8/2011 | Wagner et al. | |
| 8,187,329 B2 | 5/2012 | Theofilos | |
| 8,206,423 B2 | 6/2012 | Siegal | |
| 8,216,312 B2 * | 7/2012 | Gray | A61F 2/4455 623/17.11 |
| 8,236,029 B2 | 8/2012 | Siegal | |
| 8,241,328 B2 | 8/2012 | Siegal | |
| 8,246,622 B2 | 8/2012 | Siegal et al. | |
| 8,323,342 B2 | 12/2012 | Schwab | |
| 8,328,812 B2 | 12/2012 | Siegal et al. | |
| 8,336,559 B2 | 12/2012 | Kallabat et al. | |
| 8,337,559 B2 | 12/2012 | Hansell et al. | |
| 8,343,219 B2 | 1/2013 | Allain et al. | |
| 8,349,015 B2 | 1/2013 | Bae et al. | |
| 8,357,200 B2 * | 1/2013 | Adl | A61F 2/442 623/17.14 |
| 8,377,133 B2 | 2/2013 | Yuan et al. | |
| 8,454,694 B2 * | 6/2013 | Armstrong | A61B 17/808 623/17.11 |
| 8,460,385 B1 | 6/2013 | Wensel | |
| 8,460,387 B2 | 6/2013 | Theofilos | |
| 8,465,524 B2 | 6/2013 | Siegal | |
| 8,470,044 B2 * | 6/2013 | Bertholet | A61F 2/442 623/17.16 |
| 8,480,747 B2 * | 7/2013 | Melkent | A61F 2/4684 623/17.16 |
| 8,486,109 B2 | 7/2013 | Siegal | |
| 8,491,658 B1 * | 7/2013 | Etminan | A61F 2/4455 623/17.16 |
| 8,496,691 B2 | 7/2013 | Blain | |

(56) References Cited

U.S. PATENT DOCUMENTS

| | | | |
|---|---|---|---|
| 8,496,708 B2* | 7/2013 | Blain | A61F 2/447 623/17.16 |
| 8,500,783 B2* | 8/2013 | Baynham | A61B 17/8009 606/282 |
| 8,551,175 B1 | 10/2013 | Wensel | |
| 8,562,651 B2* | 10/2013 | Metcalf | A61B 17/7055 606/264 |
| 8,597,330 B2 | 12/2013 | Siegal | |
| 8,613,772 B2* | 12/2013 | Bray | A61F 2/4455 623/17.16 |
| 8,617,245 B2 | 12/2013 | Brett | |
| 8,628,578 B2* | 1/2014 | Miller | A61F 2/4425 623/17.16 |
| 8,641,765 B2* | 2/2014 | Muhanna | A61F 2/4455 623/17.16 |
| 8,672,977 B2 | 3/2014 | Siegal et al. | |
| 8,690,928 B1* | 4/2014 | Walkenhorst | A61B 17/7059 606/287 |
| 8,690,948 B2* | 4/2014 | Armstrong | A61F 2/4611 623/17.16 |
| 8,747,443 B2 | 6/2014 | Aferzon | |
| 8,758,439 B2* | 6/2014 | Linares | A61B 17/7043 623/17.11 |
| 8,777,993 B2 | 7/2014 | Siegal et al. | |
| 8,821,555 B2 | 9/2014 | Bae et al. | |
| 8,845,638 B2 | 9/2014 | Siegal et al. | |
| 8,900,235 B2 | 12/2014 | Siegal | |
| 8,906,098 B2 | 12/2014 | Siegal | |
| 8,932,359 B2 | 1/2015 | Brett | |
| 8,956,416 B2 | 2/2015 | McCarthy | |
| 9,005,293 B2 | 4/2015 | Moskowitz et al. | |
| 9,005,295 B2 | 4/2015 | Kueenzi et al. | |
| 9,017,408 B2 | 4/2015 | Siegal et al. | |
| 9,017,413 B2 | 4/2015 | Siegal et al. | |
| 9,039,768 B2 | 5/2015 | Voellmicke | |
| 9,044,334 B2 | 6/2015 | Siegal et al. | |
| 9,138,330 B2 | 9/2015 | Hansell et al. | |
| 9,192,419 B2 | 11/2015 | McDonough et al. | |
| 9,248,028 B2 | 2/2016 | Gamache | |
| 9,254,138 B2 | 2/2016 | Siegal et al. | |
| 9,265,546 B2 | 2/2016 | Blain | |
| 9,265,621 B2 | 2/2016 | Voellmicke | |
| 9,271,836 B2* | 3/2016 | Pavento | A61B 17/7059 |
| 9,278,009 B2 | 3/2016 | Bray et al. | |
| 9,283,092 B2 | 3/2016 | Siegal et al. | |
| 9,289,311 B1 | 3/2016 | Whipple | |
| 9,364,272 B2 | 6/2016 | Binder et al. | |
| 9,402,735 B2 | 8/2016 | McDonough et al. | |
| 9,402,738 B2 | 8/2016 | Niemiec et al. | |
| 9,408,712 B2 | 8/2016 | Siegal et al. | |
| 9,492,286 B2 | 11/2016 | Biedermann et al. | |
| 9,592,129 B2 | 3/2017 | Slivka et al. | |
| 9,662,225 B2* | 5/2017 | Pavento | A61B 17/7059 |
| 9,668,877 B2* | 6/2017 | Pavento | A61F 2/442 |
| 9,848,992 B2 | 12/2017 | McDonough et al. | |
| 9,872,781 B2* | 1/2018 | Pavento | A61F 2/4455 |
| 10,327,915 B2* | 6/2019 | Pavento | A61F 2/30744 |
| 2001/0031968 A1 | 10/2001 | Dorchak et al. | |
| 2002/0029044 A1 | 3/2002 | Monassevitch et al. | |
| 2002/0029082 A1 | 3/2002 | Muhanna | |
| 2002/0095155 A1 | 7/2002 | Michelson | |
| 2002/0099376 A1 | 7/2002 | Michelson | |
| 2002/0138146 A1 | 9/2002 | Jackson | |
| 2002/0143328 A1 | 10/2002 | Shluzas et al. | |
| 2002/0151976 A1 | 10/2002 | Foley et al. | |
| 2002/0156475 A1* | 10/2002 | Lerch | A61B 17/688 606/70 |
| 2003/0004576 A1 | 1/2003 | Thalgott | |
| 2003/0023305 A1 | 1/2003 | McKay | |
| 2003/0028197 A1 | 2/2003 | Hanson et al. | |
| 2003/0045940 A1 | 3/2003 | Eberlein et al. | |
| 2003/0050645 A1 | 3/2003 | Parker et al. | |
| 2003/0083748 A1 | 5/2003 | Lee et al. | |
| 2003/0100949 A1 | 5/2003 | Michelson | |
| 2003/0125739 A1 | 7/2003 | Bagga et al. | |
| 2003/0130739 A1 | 7/2003 | Gerbec et al. | |
| 2003/0153975 A1 | 8/2003 | Byrd et al. | |
| 2003/0158555 A1 | 8/2003 | Sanders et al. | |
| 2003/0187440 A1 | 10/2003 | Richelsoph et al. | |
| 2003/0187506 A1 | 10/2003 | Ross et al. | |
| 2003/0195632 A1 | 10/2003 | Foley et al. | |
| 2003/0225409 A1* | 12/2003 | Freid | A61B 17/7059 606/281 |
| 2004/0024464 A1 | 2/2004 | Errico et al. | |
| 2004/0034430 A1 | 2/2004 | Falahee | |
| 2004/0092929 A1 | 5/2004 | Zindrick | |
| 2004/0106996 A1 | 6/2004 | Liu et al. | |
| 2004/0111089 A1 | 6/2004 | Stevens et al. | |
| 2004/0117022 A1 | 6/2004 | Marnay et al. | |
| 2004/0127902 A1 | 7/2004 | Suzuki et al. | |
| 2004/0127990 A1 | 7/2004 | Bartish et al. | |
| 2004/0138662 A1 | 7/2004 | Landry et al. | |
| 2004/0153065 A1 | 8/2004 | Lim | |
| 2004/0153072 A1 | 8/2004 | Bonutti | |
| 2004/0167625 A1 | 8/2004 | Beyar et al. | |
| 2004/0193269 A1 | 9/2004 | Fraser et al. | |
| 2004/0199253 A1 | 10/2004 | Link et al. | |
| 2004/0199254 A1 | 10/2004 | Louis et al. | |
| 2004/0210219 A1 | 10/2004 | Bray | |
| 2004/0249377 A1 | 12/2004 | Kaes et al. | |
| 2004/0254644 A1 | 12/2004 | Taylor | |
| 2004/0260286 A1 | 12/2004 | Ferree | |
| 2005/0015147 A1 | 1/2005 | Schwardt et al. | |
| 2005/0021144 A1 | 1/2005 | Malberg et al. | |
| 2005/0033433 A1 | 2/2005 | Michelson | |
| 2005/0038513 A1 | 2/2005 | Michelson | |
| 2005/0043800 A1 | 2/2005 | Paul et al. | |
| 2005/0065608 A1 | 3/2005 | Michelson | |
| 2005/0071006 A1 | 3/2005 | Kirschman | |
| 2005/0071008 A1 | 3/2005 | Kirschman | |
| 2005/0085913 A1 | 4/2005 | Fraser et al. | |
| 2005/0096657 A1* | 5/2005 | Autericque | A61B 17/8052 623/17.11 |
| 2005/0101960 A1* | 5/2005 | Fiere | A61F 2/4611 623/17.11 |
| 2005/0113920 A1 | 5/2005 | Foley et al. | |
| 2005/0143749 A1 | 6/2005 | Zalenski et al. | |
| 2005/0143827 A1 | 6/2005 | Globerman et al. | |
| 2005/0149192 A1 | 7/2005 | Zucherman et al. | |
| 2005/0149193 A1 | 7/2005 | Zucherman et al. | |
| 2005/0154391 A1 | 7/2005 | Doherty et al. | |
| 2005/0159813 A1* | 7/2005 | Molz, IV | A61F 2/4611 623/17.11 |
| 2005/0159819 A1 | 7/2005 | McCormack et al. | |
| 2005/0165483 A1 | 7/2005 | Ray et al. | |
| 2005/0177240 A1 | 8/2005 | Blain | |
| 2005/0177245 A1* | 8/2005 | Leatherbury | A61F 2/4465 623/23.5 |
| 2005/0182416 A1 | 8/2005 | Lim et al. | |
| 2005/0209696 A1 | 9/2005 | Lin et al. | |
| 2005/0251260 A1 | 11/2005 | Gerber et al. | |
| 2005/0261768 A1 | 11/2005 | Trieu | |
| 2005/0277938 A1 | 12/2005 | Parsons | |
| 2005/0278036 A1 | 12/2005 | Leonard et al. | |
| 2006/0025860 A1 | 2/2006 | Li | |
| 2006/0030851 A1 | 2/2006 | Bray et al. | |
| 2006/0058801 A1 | 3/2006 | Schlienger et al. | |
| 2006/0079961 A1 | 4/2006 | Michelson | |
| 2006/0085071 A1 | 4/2006 | Lechmann et al. | |
| 2006/0129424 A1 | 6/2006 | Chan | |
| 2006/0142765 A9 | 6/2006 | Dixon et al. | |
| 2006/0142858 A1 | 6/2006 | Colleran et al. | |
| 2006/0142863 A1 | 6/2006 | Fraser et al. | |
| 2006/0152863 A1 | 7/2006 | Freitag et al. | |
| 2006/0178745 A1 | 8/2006 | Bartish et al. | |
| 2006/0211952 A1 | 9/2006 | Kennedy, II | |
| 2006/0229609 A1* | 10/2006 | Wang | A61B 17/7023 606/257 |
| 2006/0229724 A1 | 10/2006 | Lechmann et al. | |
| 2006/0229729 A1 | 10/2006 | Gordon et al. | |
| 2006/0235403 A1 | 10/2006 | Blain | |
| 2006/0235409 A1* | 10/2006 | Blain | A61B 17/7059 606/71 |

(56) References Cited

U.S. PATENT DOCUMENTS

| | | |
|---|---|---|
| 2006/0235411 A1 | 10/2006 | Blain et al. |
| 2006/0235518 A1* | 10/2006 | Blain ............... A61B 17/7059 623/17.11 |
| 2006/0235535 A1 | 10/2006 | Ferree et al. |
| 2006/0241597 A1 | 10/2006 | Mitchell et al. |
| 2006/0241761 A1 | 10/2006 | Gately |
| 2006/0247650 A1 | 11/2006 | Yerby et al. |
| 2006/0259147 A1 | 11/2006 | Krishna et al. |
| 2006/0265068 A1 | 11/2006 | Schwab |
| 2006/0293753 A1 | 12/2006 | Thramann |
| 2007/0049941 A1 | 3/2007 | Thramann |
| 2007/0055252 A1 | 3/2007 | Blain et al. |
| 2007/0067035 A1 | 3/2007 | Falahee |
| 2007/0073398 A1 | 3/2007 | Fabian et al. |
| 2007/0106384 A1 | 5/2007 | Bray et al. |
| 2007/0106388 A1 | 5/2007 | Michelson |
| 2007/0129804 A1 | 6/2007 | Bentley et al. |
| 2007/0162138 A1 | 7/2007 | Heinz |
| 2007/0198016 A1* | 8/2007 | Zang ...................... A61B 17/80 606/86 A |
| 2007/0213737 A1 | 9/2007 | Schermerhorn et al. |
| 2007/0213820 A1 | 9/2007 | Magerl et al. |
| 2007/0219635 A1 | 9/2007 | Mathieu et al. |
| 2007/0233118 A1 | 10/2007 | McLain |
| 2007/0233253 A1 | 10/2007 | Bray et al. |
| 2007/0233261 A1 | 10/2007 | Lopez et al. |
| 2007/0233263 A1 | 10/2007 | Melkent et al. |
| 2007/0250167 A1 | 10/2007 | Bray et al. |
| 2007/0255416 A1 | 11/2007 | Melkent et al. |
| 2007/0265631 A1 | 11/2007 | Fox |
| 2007/0270957 A1 | 11/2007 | Heinz |
| 2007/0270965 A1* | 11/2007 | Ferguson ........... A61B 17/7059 623/17.11 |
| 2007/0276490 A1* | 11/2007 | Mateyka ............ A61B 17/8004 623/17.11 |
| 2007/0282449 A1 | 12/2007 | De et al. |
| 2007/0293948 A1 | 12/2007 | Bagga et al. |
| 2007/0299521 A1 | 12/2007 | Glenn et al. |
| 2008/0015694 A1 | 1/2008 | Tribus |
| 2008/0021476 A1 | 1/2008 | Kirschman |
| 2008/0027550 A1 | 1/2008 | Link et al. |
| 2008/0033440 A1 | 2/2008 | Moskowitz et al. |
| 2008/0051890 A1* | 2/2008 | Waugh .................... A61F 2/442 623/17.11 |
| 2008/0051897 A1 | 2/2008 | Lopez et al. |
| 2008/0065219 A1 | 3/2008 | Dye |
| 2008/0077247 A1 | 3/2008 | Murillo et al. |
| 2008/0082173 A1 | 4/2008 | Delurio et al. |
| 2008/0097436 A1 | 4/2008 | Culbert et al. |
| 2008/0103597 A1 | 5/2008 | Lechmann et al. |
| 2008/0103598 A1 | 5/2008 | Trudeau et al. |
| 2008/0109005 A1 | 5/2008 | Trudeau et al. |
| 2008/0125865 A1 | 5/2008 | Abdelgany |
| 2008/0132949 A1 | 6/2008 | Aferzon et al. |
| 2008/0132958 A1 | 6/2008 | Pech et al. |
| 2008/0133012 A1 | 6/2008 | McGuckin |
| 2008/0133014 A1 | 6/2008 | Gately et al. |
| 2008/0140085 A1 | 6/2008 | Gately et al. |
| 2008/0161922 A1 | 7/2008 | Rhoda |
| 2008/0161925 A1* | 7/2008 | Brittan ................... A61F 2/4465 623/17.16 |
| 2008/0167666 A1 | 7/2008 | Fiere et al. |
| 2008/0177307 A1 | 7/2008 | Moskowitz et al. |
| 2008/0183293 A1 | 7/2008 | Parry et al. |
| 2008/0183294 A1* | 7/2008 | Adl ......................... A61F 2/442 623/17.16 |
| 2008/0221690 A1 | 9/2008 | Chaput et al. |
| 2008/0221694 A1 | 9/2008 | Warnick et al. |
| 2008/0234822 A1 | 9/2008 | Govil et al. |
| 2008/0243136 A1 | 10/2008 | Prager et al. |
| 2008/0249569 A1 | 10/2008 | Waugh et al. |
| 2008/0249575 A1 | 10/2008 | Waugh et al. |
| 2008/0249625 A1 | 10/2008 | Waugh et al. |
| 2008/0255620 A1 | 10/2008 | Strauss et al. |
| 2008/0269806 A1 | 10/2008 | Zhang et al. |
| 2008/0281425 A1 | 11/2008 | Thalgott et al. |
| 2008/0294262 A1* | 11/2008 | Levieux ................ A61F 2/4611 623/17.16 |
| 2008/0300601 A1 | 12/2008 | Fabian et al. |
| 2008/0300634 A1* | 12/2008 | Gray .................. A61B 17/7059 606/280 |
| 2008/0306596 A1 | 12/2008 | Jones et al. |
| 2008/0306598 A1 | 12/2008 | Hansen et al. |
| 2008/0312698 A1 | 12/2008 | Bergeron et al. |
| 2008/0312742 A1* | 12/2008 | Abernathie ............ A61F 2/447 623/17.16 |
| 2009/0012529 A1* | 1/2009 | Blain .................... A61F 2/4611 606/99 |
| 2009/0030421 A1 | 1/2009 | Hawkins et al. |
| 2009/0030519 A1 | 1/2009 | Falahee |
| 2009/0030520 A1 | 1/2009 | Biedermann et al. |
| 2009/0062921 A1 | 3/2009 | Michelson |
| 2009/0088849 A1 | 4/2009 | Armstrong et al. |
| 2009/0099554 A1 | 4/2009 | Forster et al. |
| 2009/0099610 A1 | 4/2009 | Johnson et al. |
| 2009/0099661 A1 | 4/2009 | Bhattacharya et al. |
| 2009/0105771 A1 | 4/2009 | Lei et al. |
| 2009/0105774 A1 | 4/2009 | Jones et al. |
| 2009/0105830 A1 | 4/2009 | Jones et al. |
| 2009/0105831 A1 | 4/2009 | Jones et al. |
| 2009/0105832 A1 | 4/2009 | Allain et al. |
| 2009/0125028 A1 | 5/2009 | Teisen et al. |
| 2009/0131988 A1 | 5/2009 | Bush et al. |
| 2009/0132054 A1 | 5/2009 | Zeegers |
| 2009/0143859 A1 | 6/2009 | McClellan et al. |
| 2009/0164020 A1 | 6/2009 | Janowski et al. |
| 2009/0182428 A1* | 7/2009 | McClellan, III ........ A61F 2/447 623/17.16 |
| 2009/0182430 A1* | 7/2009 | Tyber .................... A61F 2/4465 623/17.16 |
| 2009/0192549 A1 | 7/2009 | Sanders et al. |
| 2009/0192613 A1 | 7/2009 | Wing et al. |
| 2009/0192614 A1 | 7/2009 | Beger et al. |
| 2009/0192615 A1 | 7/2009 | Tyber et al. |
| 2009/0192616 A1 | 7/2009 | Zielinski |
| 2009/0198245 A1 | 8/2009 | Phan |
| 2009/0198287 A1 | 8/2009 | Chiu |
| 2009/0198339 A1 | 8/2009 | Kleiner et al. |
| 2009/0210062 A1 | 8/2009 | Thalgott et al. |
| 2009/0210064 A1 | 8/2009 | Lechmann et al. |
| 2009/0224023 A1 | 9/2009 | Moskowitz et al. |
| 2009/0234364 A1 | 9/2009 | Crook |
| 2009/0240333 A1 | 9/2009 | Trudeau et al. |
| 2009/0248092 A1 | 10/2009 | Bellas et al. |
| 2009/0259316 A1 | 10/2009 | Ginn et al. |
| 2009/0265007 A1 | 10/2009 | Colleran |
| 2009/0270873 A1 | 10/2009 | Fabian |
| 2009/0287251 A1 | 11/2009 | Bae et al. |
| 2009/0306779 A1* | 12/2009 | Ahn ....................... A61F 2/4465 623/17.11 |
| 2009/0326543 A1 | 12/2009 | Fabian, Jr. |
| 2009/0326580 A1* | 12/2009 | Anderson ........... A61B 17/8047 606/246 |
| 2009/0326589 A1* | 12/2009 | Lemoine ............ A61B 17/7065 606/280 |
| 2010/0004747 A1 | 1/2010 | Lin |
| 2010/0016901 A1 | 1/2010 | Robinson |
| 2010/0016973 A1 | 1/2010 | De et al. |
| 2010/0023128 A1 | 1/2010 | Malberg |
| 2010/0030334 A1* | 2/2010 | Molz, IV ............... A61F 2/4611 623/17.11 |
| 2010/0036496 A1 | 2/2010 | Yu et al. |
| 2010/0042159 A1 | 2/2010 | Butler |
| 2010/0057206 A1 | 3/2010 | Duffield et al. |
| 2010/0069969 A1 | 3/2010 | Ampuero et al. |
| 2010/0070037 A1* | 3/2010 | Parry ...................... A61F 2/44 623/17.16 |
| 2010/0078372 A1 | 4/2010 | Kerfoot |
| 2010/0087925 A1 | 4/2010 | Kostuik et al. |
| 2010/0106249 A1 | 4/2010 | Tyber et al. |
| 2010/0137987 A1 | 6/2010 | Diao et al. |
| 2010/0145457 A1 | 6/2010 | Felt et al. |

(56) References Cited

U.S. PATENT DOCUMENTS

| | | |
|---|---|---|
| 2010/0145459 A1 | 6/2010 | McDonough et al. |
| 2010/0145460 A1 | 6/2010 | McDonough et al. |
| 2010/0179656 A1 | 7/2010 | Theofilos |
| 2010/0185287 A1 | 7/2010 | Allard et al. |
| 2010/0185289 A1 | 7/2010 | Kirwan et al. |
| 2010/0185292 A1 | 7/2010 | Hochschuler et al. |
| 2010/0204739 A1 | 8/2010 | Bae et al. |
| 2010/0217325 A1 | 8/2010 | Hochschuler et al. |
| 2010/0217393 A1 | 8/2010 | Theofilos |
| 2010/0241231 A1 | 9/2010 | Marino et al. |
| 2010/0249935 A1 | 9/2010 | Slivka et al. |
| 2010/0249937 A1* | 9/2010 | Blain ............... A61F 2/447 623/17.16 |
| 2010/0256759 A1 | 10/2010 | Hansell et al. |
| 2010/0256760 A1 | 10/2010 | Hansell |
| 2010/0286777 A1 | 11/2010 | Errico et al. |
| 2010/0286781 A1* | 11/2010 | Bullard ............ A61F 2/4455 623/17.11 |
| 2010/0286783 A1 | 11/2010 | Lechmann et al. |
| 2010/0292696 A1 | 11/2010 | Chantelot et al. |
| 2010/0292737 A1 | 11/2010 | Suh |
| 2010/0305704 A1 | 12/2010 | Messerli et al. |
| 2010/0312345 A1* | 12/2010 | Duffield ........... A61F 2/4465 623/17.16 |
| 2010/0312346 A1 | 12/2010 | Kueenzi et al. |
| 2011/0009908 A1* | 1/2011 | Ferguson .......... A61F 2/4455 606/279 |
| 2011/0009966 A1 | 1/2011 | Michelson |
| 2011/0015675 A1 | 1/2011 | Howard et al. |
| 2011/0015745 A1 | 1/2011 | Bucci |
| 2011/0082550 A1* | 4/2011 | Yeh ................. A61B 17/7059 623/17.11 |
| 2011/0082555 A1 | 4/2011 | Martz et al. |
| 2011/0098747 A1 | 4/2011 | Donner et al. |
| 2011/0106159 A1 | 5/2011 | Nazeck |
| 2011/0144703 A1 | 6/2011 | Krause et al. |
| 2011/0160866 A1 | 6/2011 | Laurence et al. |
| 2011/0166656 A1 | 7/2011 | Thalgott et al. |
| 2011/0184415 A1 | 7/2011 | Anderson et al. |
| 2011/0190892 A1* | 8/2011 | Kirschman ......... A61F 2/447 623/17.16 |
| 2011/0202136 A1* | 8/2011 | Brittan ............. A61F 2/4465 623/17.16 |
| 2011/0208311 A1 | 8/2011 | Janowski |
| 2011/0213421 A1 | 9/2011 | Binder et al. |
| 2011/0230970 A1 | 9/2011 | Lynn et al. |
| 2011/0230971 A1 | 9/2011 | Donner et al. |
| 2011/0251689 A1 | 10/2011 | Seifert et al. |
| 2011/0276142 A1 | 11/2011 | Niemiec et al. |
| 2011/0282453 A1 | 11/2011 | Greenhalgh et al. |
| 2011/0319998 A1 | 12/2011 | O'Neil et al. |
| 2012/0041559 A1* | 2/2012 | Melkent ........... A61F 2/4611 623/17.11 |
| 2012/0078371 A1 | 3/2012 | Gamache et al. |
| 2012/0078372 A1 | 3/2012 | Gamache et al. |
| 2012/0078373 A1 | 3/2012 | Gamache et al. |
| 2012/0083887 A1 | 4/2012 | Purcell et al. |
| 2012/0083889 A1 | 4/2012 | Purcell et al. |
| 2012/0143336 A1 | 6/2012 | Aflatoon et al. |
| 2012/0150301 A1 | 6/2012 | Gamache et al. |
| 2012/0150303 A1* | 6/2012 | Linares ............ A61B 17/7023 623/17.16 |
| 2012/0158143 A1 | 6/2012 | Shapiro |
| 2012/0191190 A1 | 7/2012 | Trieu |
| 2012/0197401 A1 | 8/2012 | Duncan et al. |
| 2012/0203230 A1 | 8/2012 | Adams |
| 2012/0209331 A1* | 8/2012 | Michelson ........ A61B 17/025 606/264 |
| 2012/0226319 A1* | 9/2012 | Armstrong ....... A61F 2/30771 606/279 |
| 2012/0253406 A1 | 10/2012 | Bae et al. |
| 2013/0041471 A1 | 2/2013 | Siegal et al. |
| 2013/0060337 A1* | 3/2013 | Petersheim ....... A61B 17/8042 623/17.16 |
| 2013/0073044 A1 | 3/2013 | Gamache |
| 2013/0079883 A1 | 3/2013 | Butler et al. |
| 2013/0103102 A1 | 4/2013 | Taylor et al. |
| 2013/0144391 A1 | 6/2013 | Siegal et al. |
| 2013/0166027 A1* | 6/2013 | Bellas .............. A61F 2/447 623/17.16 |
| 2013/0238095 A1* | 9/2013 | Pavento ............ A61F 2/442 623/17.16 |
| 2013/0268080 A1* | 10/2013 | Melkent ........... A61F 2/442 623/17.16 |
| 2013/0310939 A1 | 11/2013 | Fabian et al. |
| 2013/0325071 A1* | 12/2013 | Niemiec ........... A61F 2/4611 606/279 |
| 2013/0345813 A1* | 12/2013 | Frank .............. A61B 17/7059 623/17.16 |
| 2014/0039623 A1* | 2/2014 | Iott ................. A61F 2/442 623/17.16 |
| 2014/0067069 A1 | 3/2014 | Lopez |
| 2014/0107786 A1* | 4/2014 | Geisler ............ A61F 2/4455 623/17.16 |
| 2014/0114415 A1* | 4/2014 | Tyber .............. A61B 17/7059 623/17.16 |
| 2014/0135930 A1 | 5/2014 | Georges |
| 2014/0142705 A1* | 5/2014 | Duffield .......... A61F 2/442 623/17.16 |
| 2014/0156009 A1* | 6/2014 | Armstrong ....... A61F 2/30771 623/17.16 |
| 2014/0172103 A1* | 6/2014 | O'Neil ............ A61F 2/4611 623/17.16 |
| 2014/0336771 A1 | 11/2014 | Zambiasi et al. |
| 2014/0364917 A1 | 12/2014 | Sandstrom et al. |
| 2015/0230929 A1 | 8/2015 | Lorio |
| 2015/0297356 A1 | 10/2015 | Gamache et al. |
| 2015/0313721 A1 | 11/2015 | Gamache et al. |
| 2015/0374511 A1* | 12/2015 | Pavento ........... A61F 2/442 623/17.16 |
| 2016/0045325 A1 | 2/2016 | Bellas et al. |
| 2016/0128846 A1 | 5/2016 | Voellmicke |
| 2016/0213487 A1 | 7/2016 | Wilson et al. |
| 2016/0317317 A1 | 11/2016 | Marchek et al. |
| 2016/0324660 A1* | 11/2016 | Pavento ........... A61B 17/7059 |
| 2016/0324662 A1 | 11/2016 | McDonough et al. |
| 2017/0065427 A1 | 3/2017 | Songer |
| 2017/0224493 A1* | 8/2017 | Pavento ........... A61F 2/447 |
| 2017/0304068 A1 | 10/2017 | Bellas et al. |
| 2017/0312090 A1 | 11/2017 | Sharabani et al. |
| 2018/0125672 A1* | 5/2018 | Pavento ........... A61F 2/4455 |

FOREIGN PATENT DOCUMENTS

| | | |
|---|---|---|
| EP | 1609444 A1 | 12/2005 |
| EP | 1683490 A2 | 7/2006 |
| EP | 1774926 A2 | 4/2007 |
| EP | 1459711 B1 | 7/2007 |
| EP | 1847240 A1 | 10/2007 |
| EP | 1506753 B1 | 9/2009 |
| FR | 2894130 A1 | 6/2007 |
| GB | 2220729 A | 1/1990 |
| GB | 2457673 A | 8/2009 |
| JP | 2006-524114 A | 10/2006 |
| JP | 2007-516808 | 6/2007 |
| JP | 2012-508044 | 4/2012 |
| WO | 98/04217 A1 | 2/1998 |
| WO | 98/34568 A1 | 8/1998 |
| WO | 99/38463 A2 | 8/1999 |
| WO | 99/52473 A1 | 10/1999 |
| WO | 01/08864 A1 | 2/2001 |
| WO | 02/13732 A2 | 2/2002 |
| WO | 03/05938 A1 | 1/2003 |
| WO | 03/05939 | 1/2003 |
| WO | 2003/003951 A1 | 1/2003 |
| WO | 03/47473 A2 | 6/2003 |
| WO | 03/70128 A1 | 8/2003 |
| WO | 03/90650 A1 | 11/2003 |
| WO | 2004/069106 A1 | 8/2004 |
| WO | 2005/020861 A1 | 3/2005 |
| WO | 2006/058281 A2 | 6/2006 |
| WO | 2006/084057 A1 | 8/2006 |

(56) References Cited

FOREIGN PATENT DOCUMENTS

| WO | 2007/003785 | A1 | | 1/2007 | |
|---|---|---|---|---|---|
| WO | 2007/098288 | A2 | | 8/2007 | |
| WO | 2007/118856 | A1 | | 10/2007 | |
| WO | 2008/149223 | A2 | | 12/2008 | |
| WO | 2009/025841 | A1 | | 2/2009 | |
| WO | 2009/064644 | A1 | | 5/2009 | |
| WO | 2009/091775 | A2 | | 7/2009 | |
| WO | 2009/136009 | A1 | | 11/2009 | |
| WO | WO-2009136009 | A1 | * | 11/2009 | ............ A61F 2/442 |
| WO | 2010/028045 | A1 | | 3/2010 | |
| WO | 2010/033786 | A2 | | 3/2010 | |
| WO | 2010/054208 | A1 | | 5/2010 | |
| WO | 2010/092893 | A1 | | 8/2010 | |
| WO | 2010/099239 | A2 | | 9/2010 | |
| WO | 2010/121028 | A2 | | 10/2010 | |
| WO | 2011/008864 | A1 | | 1/2011 | |
| WO | 2011/035126 | A1 | | 3/2011 | |
| WO | 2011/080535 | A1 | | 7/2011 | |
| WO | 2012/047712 | | | 4/2012 | |
| WO | 2012/056119 | A1 | | 5/2012 | |
| WO | 2013/018062 | A1 | | 2/2013 | |
| WO | 2013/096192 | A1 | | 6/2013 | |
| WO | 2013/191979 | A1 | | 12/2013 | |

OTHER PUBLICATIONS

Cain, "New Stand-Alone Anterior Lumbar Inerbody Fusion Device: Bioemechanical Comparison with Established Fixation Techniques", Spine, vol. 30, No. 23, pp. 2631-2636, 2005, Lippincott Williams & Wilkins, Inc.

Cohn and Younes, "Biodegradable PEO/PLA Block Copolymers", Journal of Biomaterials Research, 1988, vol. 22, pp. 993-1009.

Cohn, "Polymer Preprints", ACS Division of Polymer Chemistry, vol. 30(1), 1989, p. 498, (e.g. PEO/PLA).

Gercek, "Subsidence of Stand-Alone Cervical Cages in Anterior Interbody Fusion: Warning", Eur. Spine Journal, vol. 12, pp. 513-516, 2003, Springer-Verlag.

Heller in Handbook of Biodegradable Polymers, edited by Domb, et al, Hardwood Academic Press, pp. 99-118 (1997).

Humphries, "Anterior Fusion of the Lumbar Spine Using an Internal Fixative Device", Surgical Forum, vol. IX, pp. 770-773, American College of Surgeons, 1959, Chicago Illinois.

Kandziora, Biomechanical Comparison of Cervical Spine Interbody Fusion Cages, Spine, vol. 26, No. 17, pp. 1850-1857, 2001, Lippincott Williams & Wilkins, Inc.

Kemnitzer et al., "Degradable Polymers Derived From the Amino Acid L-Tyrozine", The Handbook of Biodegradable Polymers, edited by Domb, et al., Hardwood Academic Press, 1997, pp. 251-272.

Oxland, "A Comparative Biomechanical Investigation of Anterior Lumbar Interbody Cages: Central and Bilateral Approaches", The Journal of Bone and Joint Surgery, pp. 383-393, vol. 82A, No. 3, Mar. 2000.

Pavlov, "Good Outcome and Restoration of Lordosis After Anterior Lumbar Interbody Fusion With Additional Posterior Fixation", Spine, vol. 29, No. 17, pp. 1893-1900, 2004, Lippincott Williams & Wilkins.

Pederson, "Thermal Assembly of a Biomimetic Mineral/Collagen Composite", Biomaterials, 2003, vol. 2, pp. 4881-4890, Elsevier.

Samandouras, "A New Anterior Cervical Instrumentation System Combining an Intradiscal Cage With an Integrated Plate", Spine, vol. 26, No. 10, pp. 1188-1192, 2001, Lippincott Williams and Watkins, Inc.

Schmiedberg, "Isolation and characterization of metallic wear debris from a dynamic intervertebral disc prosthesis", J. Biomed. Mater. Res., vol. 28, Issue 11, 1277-1288, Nov. 1994.

Vandorpe, "Biodegradable Polyphosphazenes for Biomedical Applications", The Handbook of Biodegradable Polymers, edited by Domb et al., Hardwood Academic Press, 1997, pp. 161-182.

U.S. Appl. No. 13/673,061, filed Nov. 6, 2012, entitled Interbody Device With Opening to Allow Packing Graft and Other Biologies.

* cited by examiner

NUBBED PLATE

CROSS-REFERENCE TO RELATED APPLICATIONS

This is a continuation application of U.S. patent application Ser. No. 15/846,344 filed Dec. 19, 2017, which is a continuation application of U.S. patent application Ser. No. 15/581,571 filed Apr. 28, 2017, which is a continuation application of U.S. patent application Ser. No. 14/845,481, filed Sep. 4, 2015, which is a continuation of U.S. patent application Ser. No. 13/413,264 filed Mar. 6, 2012, the disclosures of each of which are hereby incorporated by reference as if set forth in their entirety herein.

BACKGROUND OF THE INVENTION

A lateral access approach is frequently selected to deliver intervertebral fusion cages to the lumbar spine. Compared to conventional anterior or posterior approaches to the lumbar spine, the lateral approach is thought to minimize posterior and/or anterior tissue damage as well as reduce surgery time, associated blood loss, vascular damage and infection risk.

In general, it is known in the art to mount a laterally-placed fusion cage with a plate that secures to the sides of adjacent vertebral bodies. This plate attaches to a side of each vertebral body adjacent the operative disc space. The primary purpose of the plate is to reduce the patient's ability to undergo excessive extension, thereby eliminating the need for the surgeon to implant posterior fixation.

U.S. Pat. No. 7,594,931 (Louis) discloses an intervertebral arthrodesis implant for insertion in an intervertebral space separating opposite faces of two adjacent vertebrae. The implant has a ring-shaped intervertebral cage having a bar that extends perpendicular to the axis of the spine. The bar has a height less than the rest of the cage. A surface of the cage contacting the vertebrae has an undulating shape for limiting sliding of the cage in a plane parallel to the vertebral faces.

PCT Published Patent Application WO2011-080535 (Dinville) discloses anchoring devices, anchoring systems for intervertebral implants, intervertebral implants, and instruments and methods for implanting the implants. In preferred configurations, these various objects share the feature of comprising or cooperating with an anchoring device having a body comprising at least one curved plate elongated along a longitudinal axis. The plate is designed to be inserted through a passage crossing at least a part of the implant in order to penetrate into at least one vertebral endplate and attach this implant onto this vertebral endplate by means of at least one stop retaining the implant. The body of the anchoring device comprises at least one longitudinal rib on at least a part of at least one of its faces, the rib being designed to cooperate with a groove made in a passage of implant.

In one type of intervertebral device suited for the lateral approach, the fusion cage is mounted with a plate that secures the cage to the adjacent vertebral bodies. In particular, US Published Patent Application 2010-0004747 (Lin) discloses a spinal fixation device comprising a trans-vertebral and intra-vertebral plate and a rectangular cage with a slot for the plate for neutralizing intervertebral movement in spinal interbody fusion. The rectangular cage with a vertical or oblique slot is inserted into the intervertebral space from the lateral or anterior side of the spinal column. The plate is then inserted through the slot of the cage and hammered into and buried inside the two adjacent vertebral bodies to achieve three-dimensional intervertebral fixation.

U.S. Pat. No. 6,432,106 (Fraser I) discloses a spinal fixation assembly includes a fusion cage to which a plate is mated. The plate is configured to receive, retain and orient bone screws.

U.S. Pat. No. 7,112,222 (Fraser II) discloses one type of prior art device that combines a cage with a plate, so that the cage is integrally bound to the plate. A representative side view of this assembly is shown in FIG. 14.

U.S. Pat. No. 7,112,222 (Fraser II) further discloses a spinal fixation assembly is provided including a fusion cage with posterior, anterior, superior, and inferior faces, and a plate having at least one aperture for receiving a bone screw and having a mating element adapted to slidably engage and mate to the anterior face of the fusion cage. The cage is adapted to be positioned between adjacent vertebrae, and the plate is effective to mate to the cage and to receive one or more bone screws to fasten the plate and secure the fusion cage to the adjacent vertebrae.

US Published Patent Application US 2011-0184415 discloses (Anderson) discloses a bone stabilization system is provided having a plate with a top and bottom surface and a hole therethrough extending along a longitudinal axis. An annular groove in the top surface encircles the axis and defines outer facing sides of a plurality of spring members integral to the plate. A plurality of slots define sides of the spring members the inward facing side of the spring members form the upper portion of the hole, which includes a first spherical portion. A fastener with a spherical portion on the fastener head extends into the hole with the spring members urged apart to allow the head to pass but restraining removal until the resistance provide by the spring members is overcome.

US Published Patent Application US 2007-0049941 discloses (Thramann) discloses a spinal fusion plate includes a means to support an adjacent vertebral segment to inhibit the adjacent vertebral segment from further degeneration. The means to support includes an attachment to an associated artificial disc or nucleus replacement, an extension, or an attachment to a bone anchor. In each case, the attachment is moveable in relation to the fusion plate to allow flexion and extension.

U.S. Pat. No. 7,887,595 (Pimenta) discloses a spinal fusion implant of non-bone construction to be introduced into an intervertebral disc space for the promotion of spinal fusion.

SUMMARY OF THE INVENTION

It has been observed by the present inventors that simply attaching a plate component against the trailing end of a lateral cage only imperfectly arrests the extension-like movement of the patient's spine. Rather, it was noticed that there was some anterior-posterior pivoting of the plate about the screw that connected the plate to the cage. See FIG. 18.

Therefore, it is an object of the present invention to provide a cage-plate assembly having a reduced ability to pivot.

In accordance with the present invention, the present inventors found that adding a separate nub component between the plate and cage, wherein the nub is attached to the plate, lessens the undesired pivotal movement of the plate. It is believed that when the nub fits snugly between the endplates of the adjacent vertebral bodies, it acts as a stop against the undesired pivotal movement of the plate.

Therefore, in accordance with the present invention, there is provided an intervertebral fusion device comprising:

a) an intervertebral fusion cage having an anterior wall, a posterior wall, leading and trailing walls connecting the anterior and posterior walls to form a central vertical throughhole, an upper surface adapted for gripping an upper endplate and a lower surface adapted for gripping a lower endplate;

b) a bone plate comprising upper and lower holes, c) a separate nub component interposed between the bone plate and the trailing wall of the cage.

DETAILED DESCRIPTION OF THE INVENTION

Figure 1:
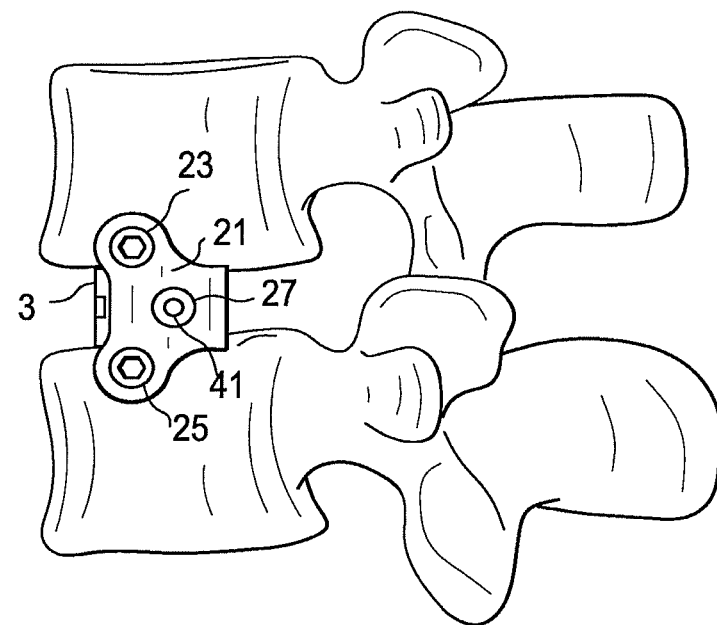
FIG. 1 shows a side view of a device of the present invention attached to sidewalls of adjacent vertebral bodies.
Figure 2:
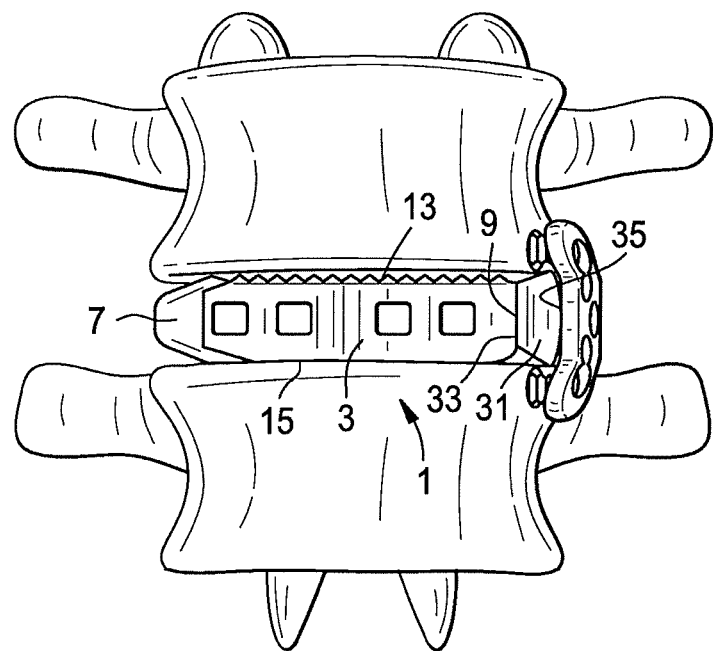
FIG. 2 shows a front view of a device of the present invention attached to sidewalls of adjacent vertebral bodies.

Now referring to FIGS. 1-6, there is provided an intervertebral fusion device comprising:

a) an intervertebral fusion cage 1 having an anterior wall 3, a posterior wall 5, a leading wall 7 and a trailing wall 9 connecting the anterior and posterior walls to form a central vertical throughhole 11, an upper surface 13 adapted for gripping an upper endplate and a lower surface 15 adapted for gripping a lower endplate;

b) a bone plate 21 comprising an upper hole 23, a lower hole 25, and a central hole 27 disposed substantially between the first and second holes, c) a nub 31 interposed between the bone plate and the trailing wall of the cage, the nub comprising:
  i) a first wall 33 contacting the trailing wall of the cage,
  ii) a second wall 35 contacting the bone plate,
  iii) a threaded throughhole 37 extending from the first wall to the second wall, and d) a threaded post 41 received in the throughhole of the nub and passing through the central hole of the bone plate.

In some embodiments, the assembly has a polyaxial joint. It is believed that the inclusion of this polyaxial joint is very advantageous to the performance of the device. It has been noticed that typical variations in human physiology often result in a situation in which the sidewalls of the adjacent vertebrae that hold the plate are not coplanar with each other. Rather, one sidewall often extends out farther than its adjacent sidewall. Thus, when a conventional cage-plate assembly (in which the plate is rigidly attached to the cage in a perpendicular relationship) is used on a typical functional spinal unit, the lack of a coplanar relationship in the vertebral sidewalls leads to a fixation situation in which only one of the vertebral sidewalls will actually contact the plate. This asymmetrical contact undesirably leads to stress concentration and poor distribution of biomechanical forces (as one screw is loaded more), leading to bony fracture.

It is believed that a polyaxial joint in the cage-plate assembly alleviates these concerns. When the cage-plate assembly of the present invention is used on a typical functional spinal unit lacking coplanar vertebral sidewalls, the plate can be polyaxially adjusted about the cage until it contacts each of the sidewalls and then locked at that desired angle. This produces a fixation in which asymmetrical contact is eliminated.

Therefore, in accordance with the present invention, there is provided an intervertebral fusion device comprising:

a) an intervertebral fusion cage having an anterior wall, a posterior wall, leading and trailing walls connecting the anterior and posterior walls to form a central vertical throughhole, an upper surface adapted for gripping an upper endplate and a lower surface adapted for gripping a lower endplate, the upper and lower surface defining a cage height;

b) a bone plate comprising a bone contacting surface, and outer surface, upper and lower holes passing from the bone-contacting surface to the outer surface, and a projection extending distally from the bone contacting surface and having a height, wherein the bone plate is connected to the trailing wall of the cage via a polyaxial connection.

Also in accordance with the present invention, there is provided an assembly device for fusing a disc space, comprising:

a) a bone plate comprising a bone-contacting inner surface, an outer surface, upper and lower holes, a central hole, each hole passing from the outer surface to the inner surface, b) an intervertebral component comprising:
  i) a first wall facing the disc space,
  ii) a second wall contacting the inner surface of the bone plate, c) first and second bone anchors passing through the upper and lower holes of the bone plate, wherein the bone plate forms a polyaxial joint with the intervertebral component.

Figure 7:
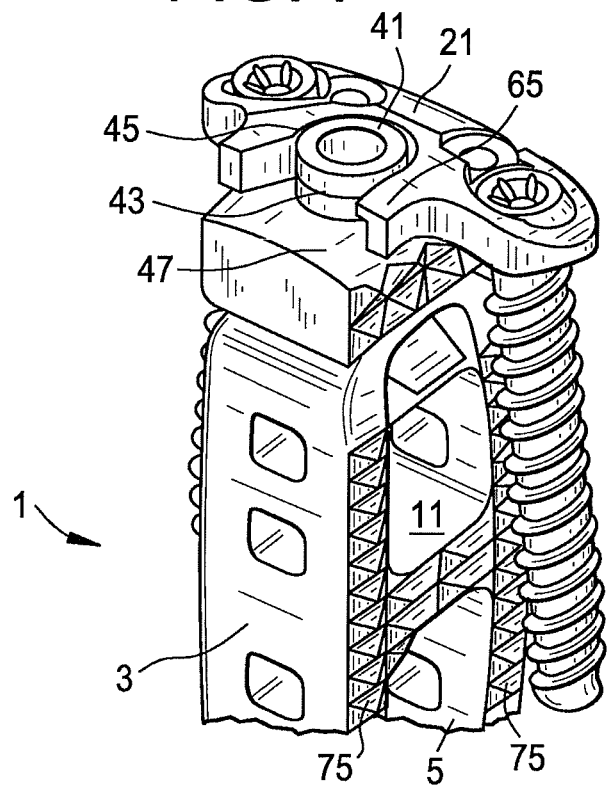
FIG. 7 discloses a perspective view of a first embodiment of a polyaxial assembly of the present invention.
Figure 8:
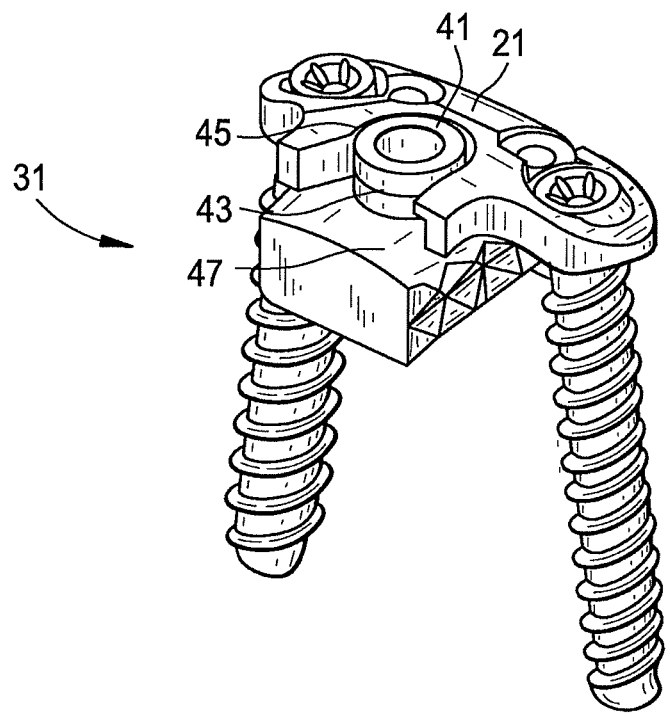
FIG. 8 discloses a perspective view of the plate and nub components of the first embodiment of a polyaxial assembly of the present invention.
Figure 10:
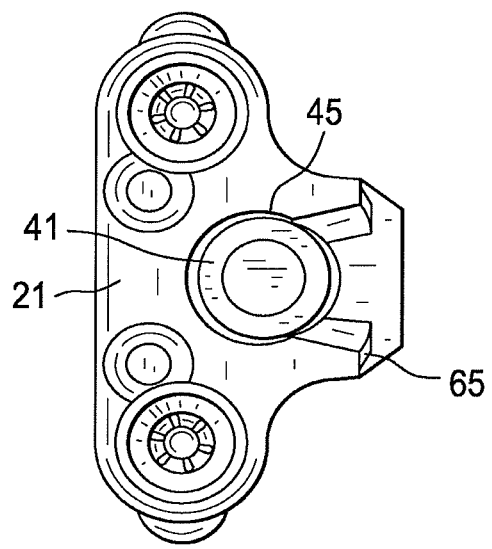
FIG. 10 shows a top view of the first embodiment of a polyaxial assembly of the present invention.

In a first polyaxial embodiment, and now referring to FIGS. 7, 8 and 10, the proximal head of the post comprises a spherical surface 43. This spherical surface can form a polyaxial joint with a mating spherical surface 45 formed in the central hole of the plate. Again, the polyaxial connection is advantageous for adjusting the orientation of the plate so that it evenly contacts both sidewalls of the adjacent vertebral bodies. Once the proper angulation is found, the post may be further threadably tightened into the nub to lock the desired angle.

Therefore, in accordance with the present invention, there is provided an interbody device for fusing a disc space, comprising:
a) a bone plate comprising a bone contacting inner surface, an outer surface, upper and lower holes, a central hole having a spherical surface thereon, each hole passing from the outer surface to the inner surface,
b) an intervertebral component comprising:
i) a first wall facing the disc space,
ii) a second wall contacting the inner surface of the bone plate,
iii) a threaded throughhole extending from the first wall to the second wall,
c) first and second bone anchors passing through the upper and lower holes of the bone plate,
d) a post having a proximal spherical head and a distal threaded shaft, wherein the inner surface of the bone plate contacts the second wall of the intervertebral component,
wherein the central hole of the bone plate and the threaded throughhole of the intervertebral component align,
wherein the distal threaded shaft of the post is threadably received in the threaded throughhole of the nub, and wherein the proximal spherical head of the post is received in the spherical surface of the central hole of the bone plate to form a polyaxial joint).

Now referring to FIGS. 7-10, in some embodiments in which the plate and post form a polyaxial joint, the second wall of the nub (which contacts the bone plate) has a convex surface 47. This convex surface is useful in the polyaxial joint embodiments of the present invention because it accommodates more tilting of the plate with respect to the nub while maintaining the joint.

Likewise, in some embodiments in which the plate and post form a polyaxial joint, the inner surface of the bone plate has a concave surface 49. This concave surface is useful in the polyaxial joint embodiments in which the second wall of the nub is convex because it accommodates more tilting of the plate with respect to the nub while maintaining the joint.

Figure 9:
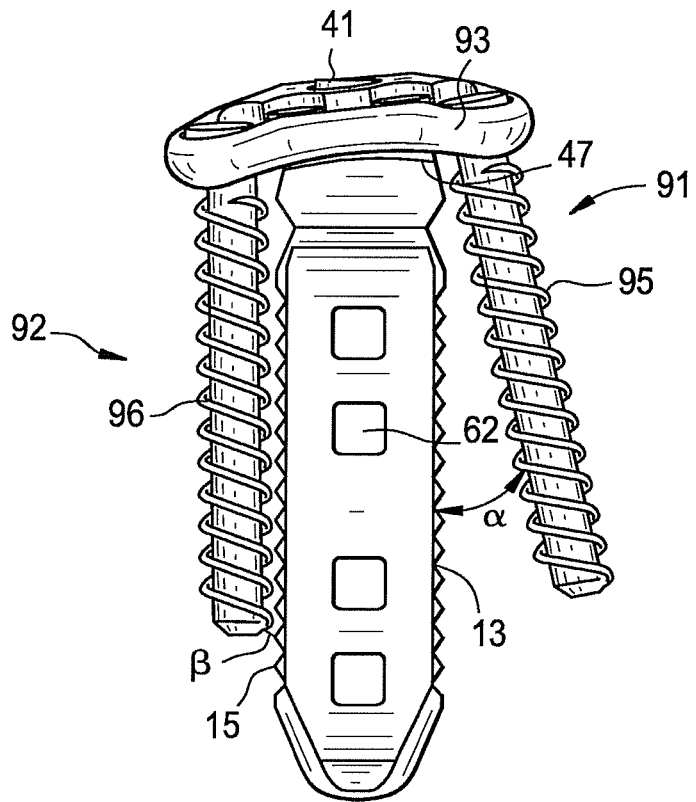
FIG. 9 shows a side view of the first embodiment of a polyaxial assembly of the present invention.

In some embodiments, and now referring to FIG. 9, the shaft 95 of the upper bone anchor 91 and the upper surface 13 of the cage define a first angle α, the shaft 96 of the lower bone anchor 92 and the lower surface 15 of the cage define a second angle β, and the first angle α is not equal to second angle β. This condition occurs when a polyaxial joint is created between the nub and bone plate, and the adjacent vertebral bodies do not align in a co-planar manner. In some embodiments thereof, the first angle α differs from second angle β by at least 5 degrees.

Figure 11:
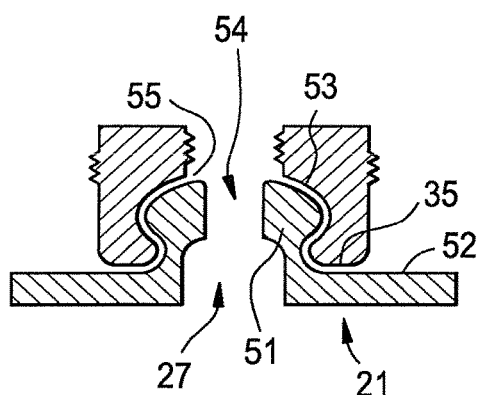
FIG. 11 discloses a cross-section view of a second embodiment of a polyaxial assembly of the present invention.
Figure 16:
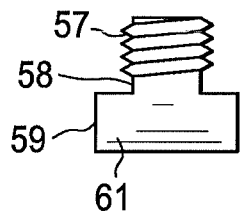
FIG. 16 discloses a threaded post of the present invention.

In a second polyaxial preferred embodiment, and now referring to FIG. 11, the plate has an annular projection 51 extending distally from its inner surface 52 about the central hole, and the nub has a recessed surface 53 extending distally about its throughhole 54 from its second wall, so that the annular projection forms a polyaxial joint 55 with the recessed surface of the nub. The polyaxial nature of the connection between the plate and nub allows the plate to float over the nub. This ability to float facilitates the plate's fit upon vertebral body sidewall surfaces that are often not aligned in a coplanar manner. A post may be added to the assembly by passing it through the plate's central hole and attaching to the nub's throughhole. Now referring to FIG. 16, a thread 57 on the post's shaft 58 allows it to threadably mate with the throughhole of the nub, while a head 59 on the proximal end portion 61 of the post allows it to loosely retain the plate upon the nub. Thus the post acts to retain the plate on the nub while allowing the polyaxial connection to retain its ability to move. Once the desired angulation is achieved, the post may be further tightened upon the assembly to lock the desired angulation.

It is believed that the device of FIG. 11 represents the first polyaxial plate known to the present inventors.

Therefore, in accordance with the present invention, there is provided an interbody device for fusing a disc space, comprising:
a) a bone plate comprising a bone contacting inner surface, an outer surface, upper and lower holes, a central hole, each hole passing from the outer surface to the inner surface, and an annular projection extending distally from the inner surface about the central hole,
b) an intervertebral component comprising:
i) a first wall facing the disc space,
ii) a second wall contacting the inner surface of the bone plate,
iii) a throughhole extending from the first wall to the second wall,
iv) a recessed surface extending distally about the throughhole,
c) first and second bone anchors passing through the upper and lower holes of the bone plate,
wherein the annular projection of the bone plate forms a polyaxial joint with the recessed surface of the intervertebral component.

In general, the cage of the present invention can be any interbody fusion cage suitable for promoting fusion between two vertebral bodies. The cage can be adapted for lumbar, cervical or thoracic use. The cage can be adapted for lateral, posterior, or anterior insertion. In some preferred embodiments, the cage is adapted for lateral approach to the lumbar spine. Typically, the cage will have an anterior wall, a posterior wall, leading and trailing walls connecting the anterior and posterior walls to form a central vertical throughhole, an upper surface adapted for gripping an upper endplate and a lower surface adapted for gripping a lower endplate. The central vertical throughhole facilitates bone growth between the two adjacent vertebral endplates. Each of the posterior and anterior walls may have ventral-dorsal throughholes 62 therethrough in order to accommodate fusion as well. The leading wall of the lateral cage may have a bulleted nose 63 that eases insertion into the disc space.

The bone plate of the present invention typically comprises a bone-contacting inner surface, an outer surface, and upper and lower holes passing from the bone-contacting surface to the outer surface. Bone anchors pass through these upper and lower holes to thereby anchor the plate to the adjacent vertebral bodies.

In some embodiments, and now referring to FIGS. 7, 8, and 10, the central hole of the plate (into which the post seats) opens laterally onto a sidewall 65 of the plate. The purpose of this lateral opening is to allow a snap-fit assembly. It is believed that when this opening constitutes about 40% of the central hole periphery, the snap fit will be sufficiently robust so as to hold plate on the post.

In some embodiments, the central hole in the plate is provided in the form of an elongated slot. The elongated slot allows for slidable adjustment of the plate upon the nub, thereby allowing for a fine tuning of the plate location after the nub location is set.

In some embodiments, the bone-contacting inner surface of the plate narrows distally. This contouring helps the plate fit between the adjacent vertebrae. This feature is believed to be advantageous in MIS procedures in which the components are inserted into the spinal area through a tube in the absence of a clear line of sight on the part of the surgeon.

Figure 13:
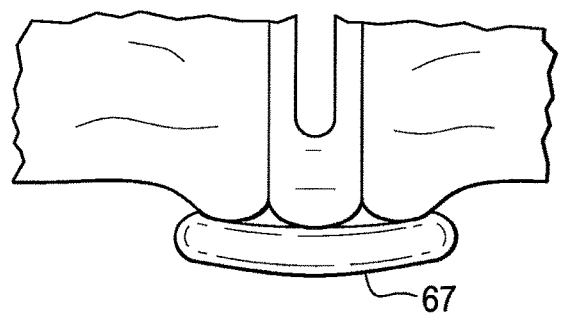
FIG. 13 shows a side view of a concave bone plate attached to both sidewalls of adjacent vertebral bodies.
Figure 14:
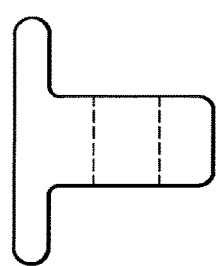
FIG. 14 discloses a side view of a conventional fusion device comprising an integral cage and plate.

In some embodiments, as in FIG. 13, the outer surface 67 of the bone plate is convex. This condition helps the plate conform to the convex bony surfaces of the adjacent vertebrae.

Figure 12:
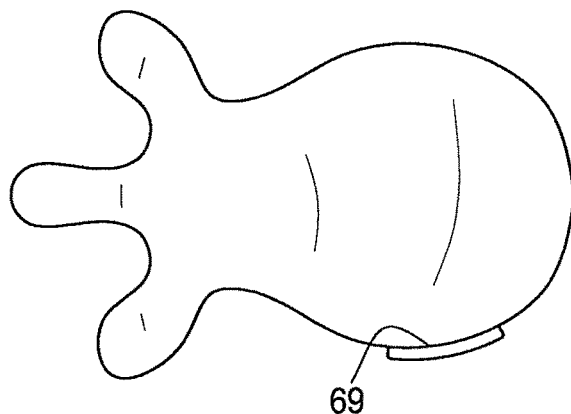
FIG. 12 shows a top view of a concave bone plate attached to a sidewall of a vertebral body.

In some embodiments, as in FIG. 12, the bone-contacting inner surface 69 of the bone plate is concave. This condition helps the plate conform to the convex bony surfaces of the adjacent vertebrae.

Figure 3:
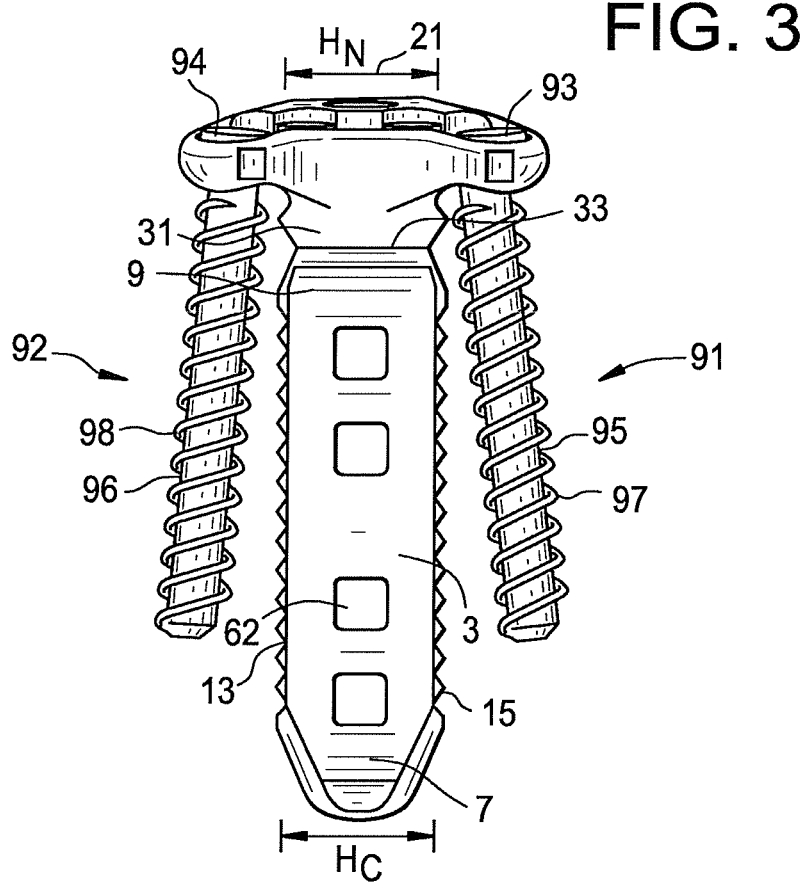
FIG. 3 shows a front view of a device of the present invention.
Figure 4:
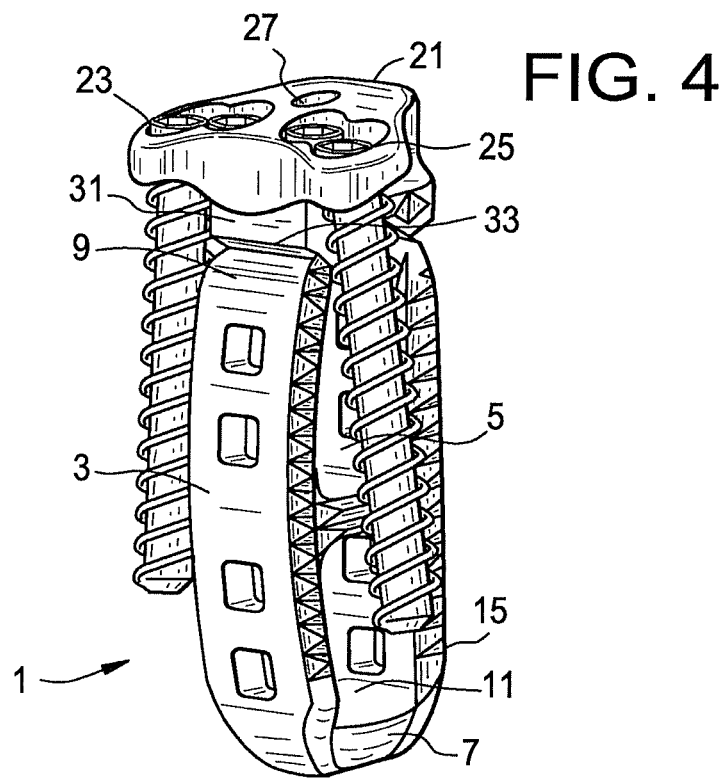
FIG. 4 shows a perspective view of a device of the present invention.

In some embodiments, as in FIG. 3, the inner surface of the plate further comprises a radius 201 and a projection 203. This radius advantageously matches the contour of the vertebral body in this region.

As discussed above, the purpose of the nub is to prevent undesired pivoting of the plate about its centerpoint.

In some embodiments, the cage, plate and nub are present as separate components. This condition maximizes the surgeon's ability to adjust the location of the plate after fixing the locations of the cage and nub.

Figure 15:
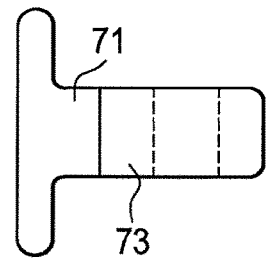
FIG. 15 is a side view of a device of the present invention in which the nub and plate are integral.

In some embodiments, and now referring to FIG. 15, the nub and plate are an integral component 71 that is separate from the cage 73.

Therefore, in accordance with the present invention, there is provided an intervertebral fusion device comprising:

a) an intervertebral fusion cage having an anterior wall, a posterior wall, leading and trailing walls connecting the anterior and posterior walls to form a central vertical throughhole, an upper surface adapted for gripping an upper endplate and a lower surface adapted for gripping a lower endplate, b) a separate bone plate component comprising a bone contacting surface, and outer surface, upper and lower holes passing from the bone-contacting surface to the outer surface, and a projection extending distally from the bone contacting surface, wherein the projection of the bone plate contacts the trailing wall of the cage.

In some embodiments, and now referring to FIGS. 7 and 8, the nub further comprises:

iii) an upper surface adapted for gripping an upper endplate, and
iv) a lower surface adapted for gripping a lower endplate
wherein each of the upper and lower surfaces of the nub is disposed between the first and second walls of the nub.

In preferred embodiments, gripping is accomplished by providing a plurality of teeth 75 upon each of the upper and lower surfaces. The purpose of these nub teeth is to enhance the snug fit of the nub between the vertebral bodies and thereby further prevent the rocking of the plate.

In some embodiments, and now referring to FIG. 3, the upper surface and lower surface of the cage define a cage height, and the lower surface and upper surface of the nub define a nub height, and wherein the nub height HN is not greater than the cage height Hc. This condition enhances the ability of the surgeon to transport the nub down the same MIS tube as the cage.

In some embodiments, the nub height is not less than the cage height. This condition enhances the snug fit of the nub between the vertebral bodies and thereby further prevent the rocking of the plate.

In some embodiments, the nub height is substantially the same as the cage height. This condition possess the attributes of the two conditions described above.

In some embodiments, and now referring to FIG. 3, the nub narrows distally. This contouring helps the nub locate the hole in the annulus through which the cage has been placed. This feature is believed to be advantageous in MIS procedures in which the components are inserted into the spinal area through a tube without the surgeon having a clear line of sight.

Figure 17:
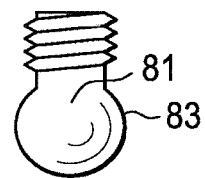
FIG. 17 discloses a post of the present invention having a spherical head.
Figure 18:
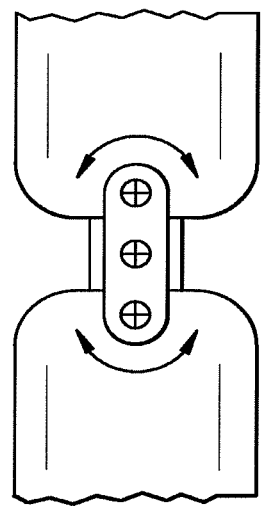
FIG. 18 discloses a side view of a conventional cage-plate assembly inserted in a disc space.

The function of the post is to retain the plate on the nub. Typically, and now referring to FIGS. 16 and 17, the post has a threaded distal end portion adapted for threadable mating to the central hole of the nub. In some embodiments, the post has a proximal end portion forming an enlarged head. In some embodiments thereof, the proximal head 81 has a spherical portion 83.

Typically, the post passes through the central hole of the plate and threads into the nub. However, in some embodiments, the post can thread into the cage as well.

Generally, and now referring to FIGS. 3 and 9, the device of the present invention also comprises upper and lower bone anchors 91,92 received in the respective upper and lower holes, each bone anchor having a proximal head 93,94 and a distal shaft 95,96. Preferably, the bone anchor is a screw that has a threaded shaft 97,98.

Figure 5:
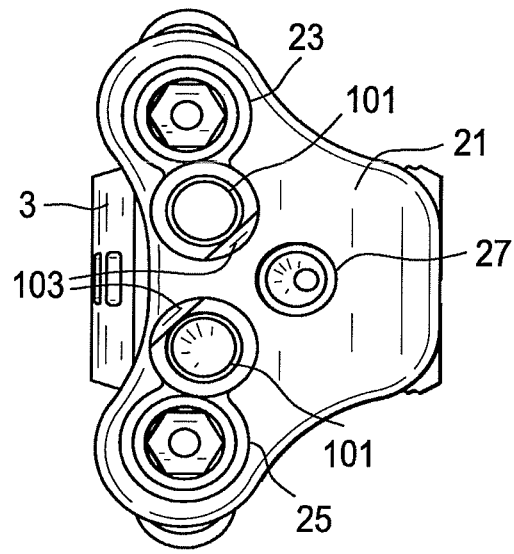
FIG. 5 shows a side view of a device of the present invention.
Figure 6:
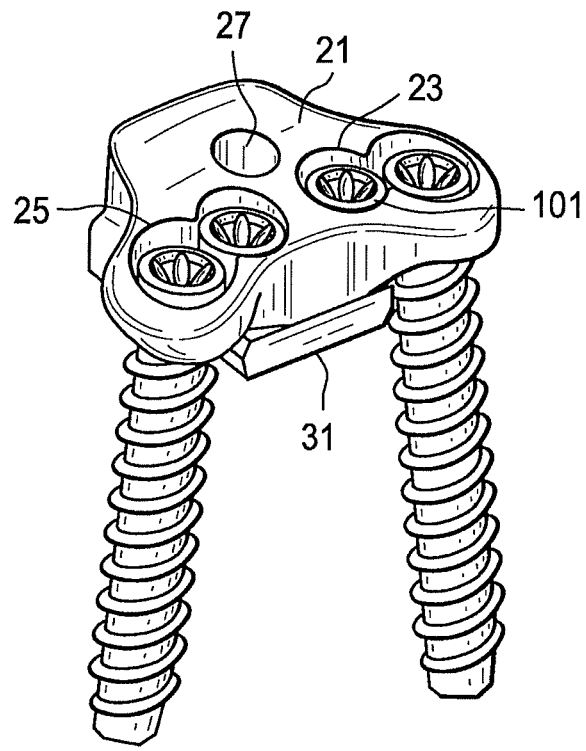
FIG. 6 shows a perspective view of a device of the present invention without its cage.

Generally, and now referring to FIGS. 5 and 6, the device of the present invention also comprises first and second cams 101 threadably received in the respective threaded recesses 103 of the bone plate and bearing against the respective heads of the bone anchors. These cams tighten against the heads of the screws, thereby preventing screw backout.

The cages of the present invention may be made from any non-resorbable material appropriate for human surgical implantation, including but not limited to, surgically appropriate metals, and non-metallic materials, such as carbon fiber composites, polymers and ceramics.

The interbody devices are preferably made out of PEEK or CFRP or any other suitable material providing adequate strength and radiolucency. However, implantable metals such as titanium or stainless steel components may be required to ensure adequate strength for either the interbody device. In some cases the interbody device can be made as a combination of PEEK and metal. In some cases, resorbable materials such as polylactide, polyglycolide, and magnesium are preferred.

In some embodiments, the cage material is selected from the group consisting of PEEK, ceramic and metallic. The cage material is preferably selected from the group consisting of metal and composite (such as PEEK/carbon fiber).

If a metal is chosen as the material of construction for a component, then the metal is preferably selected from the group consisting of titanium, titanium alloys (such as Ti-6Al-4V), chrome alloys (such as CrCo or Cr—Co—Mo) and stainless steel.

If a polymer is chosen as a material of construction for a component, then the polymer is preferably selected from the group consisting of polyesters, (particularly aromatic esters such as polyalkylene terephthalates, polyamides; polyalkenes; poly(vinyl fluoride); PTFE; polyarylethyl ketone PAEK; polyphenylene and mixtures thereof.

If a ceramic is chosen as the material of construction for a component, then the ceramic is preferably selected from the group consisting of alumina, zirconia and mixtures thereof. It is preferred to select an alumina-zirconia ceramic, such as BIOLOX Delta™, available from CeramTec of Plochingen, Germany.

In some embodiments, the cage member comprises PEEK. In others, it is a ceramic.

In some embodiments, the first component consists essentially of a metallic material, preferably a titanium alloy or a chrome-cobalt alloy.

In some embodiments, the components are made of a stainless steel alloy, preferably BioDurR CCM Plus® Alloy available from Carpenter Specialty Alloys, Carpenter Technology Corporation of Wyomissing, Pa. In some embodiments, the outer surfaces of the components are coated with a sintered beadcoating, preferably Porocoat™, available from DePuy Orthopaedics of Warsaw, Ind.

In some embodiments, the components are made from a composite comprising carbon fiber. Composites comprising carbon fiber are advantageous in that they typically have a strength and stiffness that is superior to neat polymer materials such as a polyarylethyl ketone PAEK. In some embodiments, each component is made from a polymer composite such as a PEKK-carbon fiber composite.

Preferably, the composite comprising carbon fiber further comprises a polymer. Preferably, the polymer is a polyarylethyl ketone (PAEK). More preferably, the PAEK is selected from the group consisting of polyetherether ketone (PEEK), polyether ketone ketone (PEKK) and polyether ketone (PEK). In preferred embodiments, the PAEK is PEEK.

In some embodiments, the carbon fiber comprises between 1 vol % and 60 vol % (more preferably, between 10 vol % and 50 vol %) of the composite. In some embodiments, the polymer and carbon fibers are homogeneously mixed. In others, the material is a laminate. In some embodiments, the carbon fiber is present in a chopped state. Preferably, the chopped carbon fibers have a median length of between 1 mm and 12 mm, more preferably between 4.5 mm and 7.5 mm. In some embodiments, the carbon fiber is present as continuous strands.

In especially preferred embodiments, the composite comprises: [0119] 40-99% (more preferably, 60-80 vol %) polyarylethyl ketone (PAEK), and [0120] 1-60% (more preferably, 20-40 vol %) carbon fiber, wherein the polyarylethyl ketone (PAEK) is selected from the group consisting of polyetherether ketone (PEEK), polyether ketone ketone (PEKK) and polyether ketone (PEK).

In some embodiments, the composite consists essentially of PAEK and carbon fiber. More preferably, the composite comprises 60-80 wt % PAEK and 20-40 wt % carbon fiber. Still more preferably the composite comprises 65-75 wt % PAEK and 25-35 wt % carbon fiber.

In some embodiments, the post and screw components of the present invention are made from a biocompatible metal, such as stainless steel, chromium cobalt, or titanium alloy.

In some embodiments, the plates of the present invention are made from a biocompatible metal, such as stainless steel, chromium cobalt, or titanium alloy.

Although the present invention has been described with reference to its preferred embodiments, those skillful in the art will recognize changes that may be made in form and structure which do not depart from the spirit of the invention.

In some embodiments, the central throughhole of the cage is filled with a fusion material. This fusion material promotes bony fusion of the adjacent vertebral bodies through the disc space. In some embodiments, the fusion material may be autograft bone marrow or allograft bone. In some embodiments, the fusion material may be synthetic, such as tricalcium phosphate or hydroxyapatite. In some embodiments, the fusion material may be a recombinant protein, such as a growth factor.

Implant Placement without a Plate Cage Connection

After successfully accessing, clearing and sizing the disc space, select the corresponding implant, fill the cage implant with autogenous bone graft material and attach to the inserter. Gently impact the cage implant into the disc space while monitoring placement under AP fluoroscopy. Ideal placement of the implant is to support the endplate medial/laterally to the contra-lateral rim and between the anterior third and middle third of the disc space from an anterior/posterior perspective.

Select the appropriate nubbed plate implant based on morphology and cage size, attach it to its respective inserter. Using the cage as a guide, insert the plate until the nubbed portion is within the disc space supporting the vertebral body rim and the plate portion abuts the ipsilateral walls of the superior and inferior vertebral bodies. The nubbed plate can be slightly repositioned from the cage location anteriorly or posteriorly in order to optimize the screw location or to account for anomalies such as osteophytes or a slightly compromised cage trajectory.

Attach the plate with the appropriate anchors.

Implant Placement with the Plate and Cage Connected

After successfully accessing, clearing and sizing the disc space, select the corresponding implant, fill the cage portion with autogenous bone graft material and attach the plate-cage combination to the inserter. Gently impact the implant into the disc space while monitoring placement under AP fluoroscopy. Ideal placement of the implant is for the cage portion to support the endplate medial/laterally to the contra-lateral rim and for the nubbed portion to support the ipsilateral rim while the plate portion is in contact with the walls of the superior and inferior vertebral bodies. The implant should be between the anterior third and middle third of the disc space from an anterior/posterior perspective.

The nubbed plate portion can only be slightly repositioned from the cage based on the extent of the polyaxial/sliding connection between the plate and nubbed portion. This allows for a diminished ability to accommodate morphological or surgical anomalies but increases the ergonomics of the surgery by reducing it to a single insertion technique.

Attach the plate with the appropriate anchors.

In some embodiments, the nub supports the ipsilateral rim of the vertebral body and the cage supports the contralateral rim of the vertebral body.

We claim:

1. A method of implanting an intervertebral fusion device, the method comprising the steps of:

inserting a leading end of an elongated member into an intervertebral space that is defined by an upper vertebral endplate and a lower vertebral endplate, such that an upper surface of the elongated member contacts the upper vertebral endplate, and a lower surface opposite the upper surface along a vertical direction contacts the lower vertebral endplate, wherein the elongated member further defines a trailing end and a vertical through hole that extends therethrough; and moving a body about a component along a curved path, wherein the component is interposed between the body and the elongated member and separate from both the body and the elongated member, such that the component faces the trailing end of the elongated member, wherein a threaded member extends through the body.

2. The method as recited in claim 1, wherein the moving step comprises sliding the body along a convex outer surface of the component.

3. The method as recited in claim 2, wherein an entirety of the convex outer surface is convex.

4. The method as recited in claim 1, wherein the threaded member comprises a threaded shaft.

5. The method as recited in claim 4, wherein the threaded shaft extends into the component.

6. The method as recited in claim 1, wherein the vertical through hole extends through the elongated member along a vertical direction, the component has a height along the vertical direction, the elongated member has a height along the vertical direction, and the height of the component is no greater than the height of the elongated member.

7. The method as recited in claim 1, wherein the component is in contact with the elongated member.

8. The method as recited in claim 1, further comprising the step of locking the body to the component so as to prevent movement of the body about the component when the body is in a locked state.

9. The method as recited in claim 8, wherein the moving step comprising siding the body along the component when the body is in an unlocked state.

10. The method as recited in claim 9, further comprising the step of tightening the threaded member against the body so as to define the locked state.

11. The method as recited in claim 1, further comprising the step of limiting, via a stop surface, movement of the body about the component.

12. The method as recited in claim 1, further comprising the step of limiting, via a stop surface defined by a surface of the component, movement of a concave inner surface of the body about a complementary convex outer surface of the component.

13. The method as recited in claim 1, wherein the threaded member is centrally located in the body.

14. The method as recited in claim 1, wherein the moving step further comprises moving the body with respect to the elongated member.

15. The method as recited in claim 1, further comprising the step of gripping the upper vertebral endplate and the lower vertebral endplate, respectively, with respective teeth of the upper surface and the lower surface.

16. The method as recited in claim 1, wherein the component comprises a nub.

17. The method as recited in claim 1, wherein the component defines a surface that faces the body, the surface defines a pair of opposed terminal ends, and the surface is curved from one of the terminal ends to the other of the terminal ends.

18. The method as recited in claim 17, wherein the moving step comprises guiding the body to move along a path parallel to the surface.

19. The method as recited in claim 1, further comprising the step of driving a threaded shaft of a bone screw into one of an upper vertebra and a lower vertebra that define the upper vertebral endplate and the lower vertebral endplate, respectively.

20. The method as recited in claim 19, wherein the driving step comprises driving a first bone screw into the upper vertebra, and driving a second bone screw into the lower vertebra.

* * * * *